United States Patent [19]

Derouin et al.

[11] Patent Number: 5,681,314
[45] Date of Patent: Oct. 28, 1997

[54] CUTTING A BONE GRAFT

[75] Inventors: James D. Derouin, Taunton; William J. Reimels, Scituate, both of Mass.; Lawrence M. Shall, 1324 Baecher La., Norfolk, Va. 23509

[73] Assignee: Lawrence M. Shall, Norfolk, Va.

[21] Appl. No.: 666,123

[22] Filed: Jun. 21, 1996

[51] Int. Cl.⁶ .................................................. A61B 17/15
[52] U.S. Cl. ........................ 606/79; 606/82; 606/84; 606/87; 606/88
[58] Field of Search ........................ 606/79, 80, 82, 606/84, 86, 87, 88, 96; 623/13

[56] References Cited

U.S. PATENT DOCUMENTS

| 4,600,005 | 7/1986 | Hendel. |
| 5,092,875 | 3/1992 | McLees. |
| 5,320,115 | 6/1994 | Kenna. |

OTHER PUBLICATIONS

Kaltec HTS–Ligament Graft Harvesting System, Dr. P.J. Dobson, F.R.A.C.S., Orthopaedic Surgeon, Adelaide, South Australia.
Smith & Nephew Dyonics Inc., Patella Tendon Bone Plug Harvesting Saw, 1990.
"Patellar Tendon Bone Block Harvesting", Arthrex.
William G. Carson, Jr., M.D., "The Concept Patellar Tendon Graft Guide Surgical Technique", Concept, Largo, Florida, 1991.
"A Unique Method for Harvesting Central Third Bone–Patellar Tendon–Bone Grafts With Cylindrical Bone Plugs", The Graftologer, Neoligaments, Ltd., Leeds, U.K.

*Primary Examiner*—Michael Buiz
*Assistant Examiner*—David O. Reip
*Attorney, Agent, or Firm*—Kaufman & Canoles

[57] ABSTRACT

A guide and other tools for cutting a bone graft from, e.g., the patella. The guide includes a guiding portion configured to engage a bone cutting instrument (such as a saw with a curved cutting surface), and a bone-engaging portion insertable into a cut in the surface of the bone to position the guiding portion in a selected orientation with respect to the bone. During use, the guiding portion directs the bone cutting instrument to cut the graft in the selected orientation. One of the other tools used with the guide is a spacer which has a bone-engageable portion insertable into the cut in the bone surface, and a surface arranged with respect to the bone-engageable portion and configured to guide a saw in making a second cut in the bone surface parallel to the first-mentioned cut. The guide includes a housing that supports the guiding portion, and arms secured to the housing and on which the bone-engaging portions of the guide are disposed. Another one of the tools used with the guide is a clamp which clamps the guide housing to the bone.

29 Claims, 6 Drawing Sheets

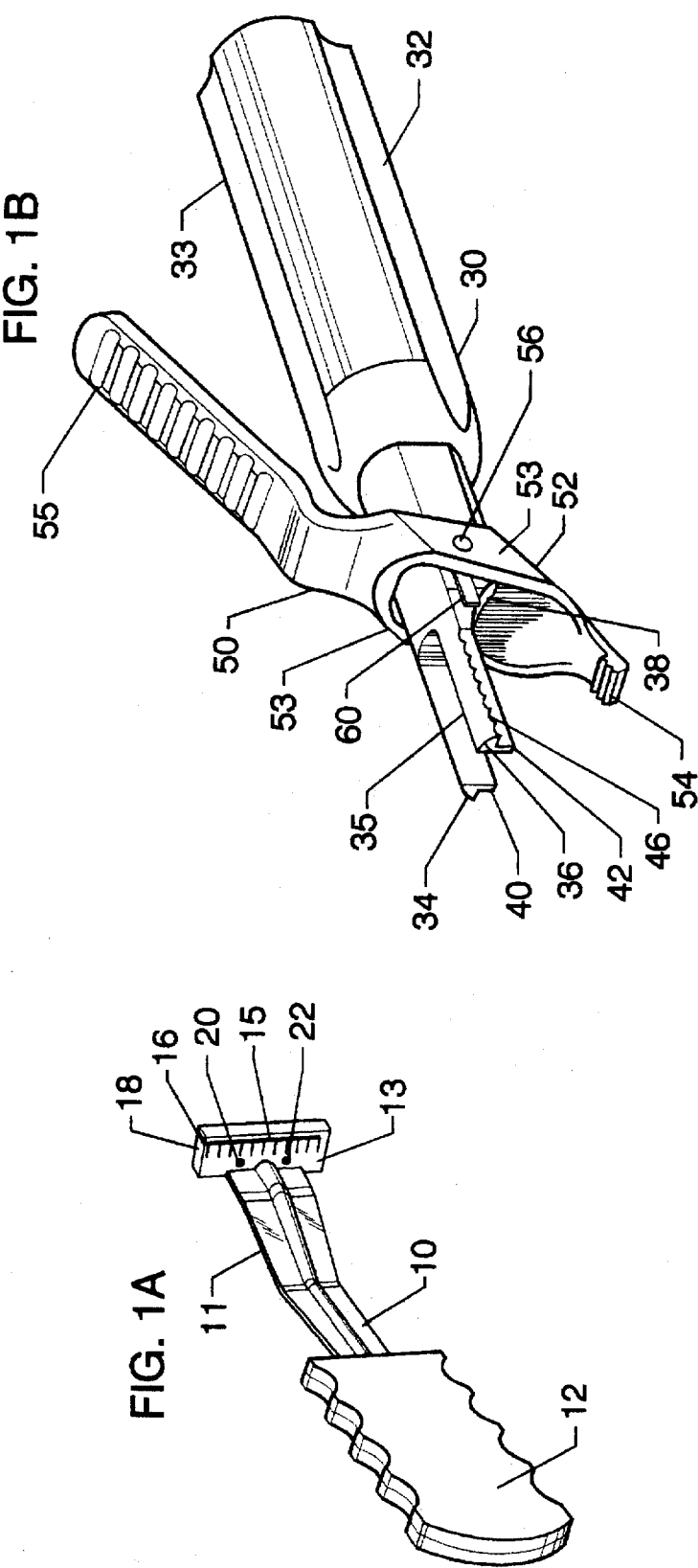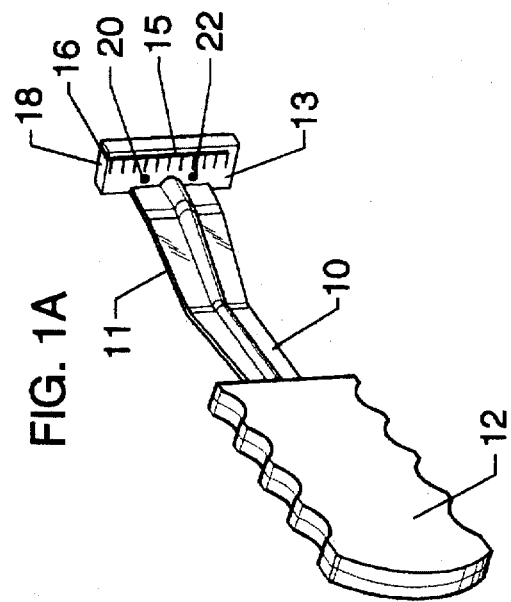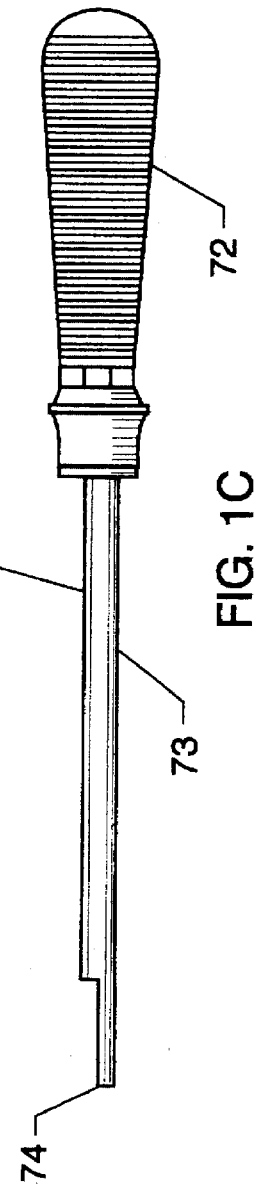

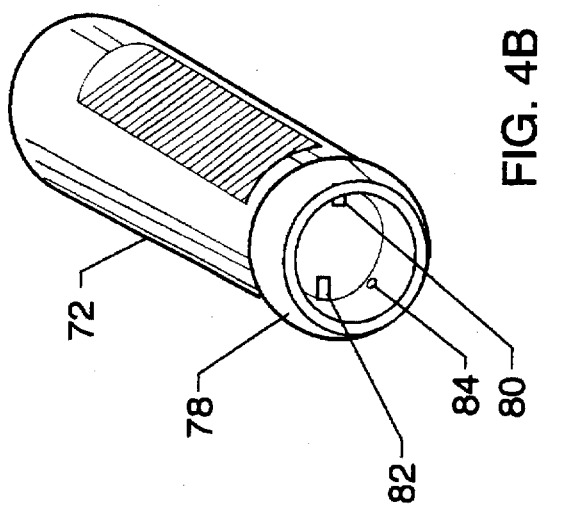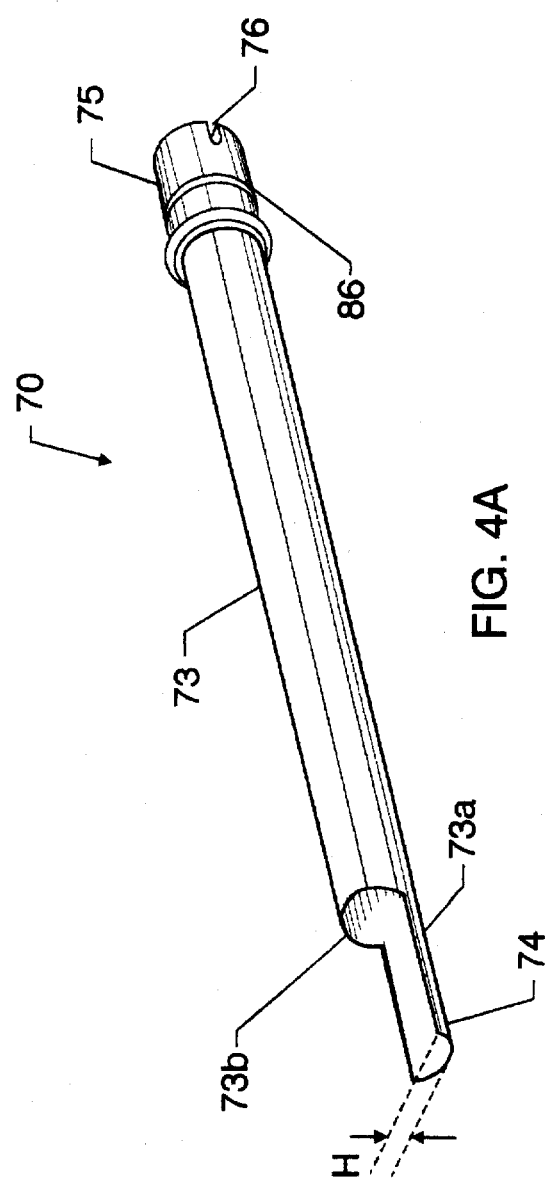

CUTTING A BONE GRAFT

BACKGROUND OF THE INVENTION

This application relates to cutting a graft from a bone, such as the patella.

A damaged anterior cruciate ligament (ACL) is often replaced with a portion (such as a strip that includes the middle one-third) of the patellar tendon. The patellar tendon strip often is removed with its ends still attached to small segments of the patella and the tibia. Typically, these bone segments are removed from the underlying bone using an osteotome (which resembles a chisel) or a saw. The segments serve as bone grafts which anchor the ends of the patellar tendon strip within tunnels in the tibia and femur (generally, the bone segments are initially secured within the tunnels by devices such as interference screws and fuse with the tibia and femur within a short period after surgery).

SUMMARY OF THE INVENTION

This invention features a guide and other instruments for cutting bone grafts smoothly, accurately, and quickly.

In one general aspect of the invention, the guide includes a guiding portion configured to engage a bone cutting instrument, and a bone-engaging portion insertable into a cut in the surface of the bone to position the guiding portion in a selected orientation with respect to the bone. In use, the guiding portion directs the bone cutting instrument to cut the graft in the selected orientation.

Preferred embodiments may include one or more of the following features.

One of the other instruments used with the guide is a spacer which has a bone-engageable portion insertable into the cut in the bone surface, and a surface arranged with respect to the bone-engageable portion and configured to guide a saw in making a second cut in the bone surface parallel to the first-mentioned cut. The spacer includes a plate which is placed on the bone, and the surface is the edge of a slot in the plate. The bone-engageable portion is a flange that protrudes from the plate. Markings are disposed on the plate adjacent to the slot to indicate the length of the second cut.

The guide has a second bone-engaging portion insertable into the second cut. The bone-engaging portions of the guide are arranged along the selected orientation so that the guiding portion directs the cutting instrument to cut the graft between a first and second ends of the cuts. The spacer also includes a second surface arranged transversely to the bone-engageable portion and configured to guide a saw making a third cut in the bone transverse to the first and second cuts at the second end of the cuts. The spacing between the first and second cuts defines the width of the bone graft; the third cut defines the maximum length of the graft.

One or more holes may be provided in the spacer for exposing areas of bone surface under the spacer. This feature enables, for example, suture holes to be formed at precise positions in the underlying bone with the spacer in place.

The guide includes a housing that supports the guiding portion, and an arm secured to the housing and on which the bone-engaging portion of the guide is disposed. Preferably, the guiding portion is an opening arranged in the selected orientation in the housing, and the arm extends from the housing in the selected orientation. The bone-engaging portion of the guide includes a rail disposed on the underside of the arm. The underside of the arm is also equipped with a ridged surface adjacent to the rail and engageable with the bone surface when the rail is inserted into the cut. Markings on the upper surface of the arm indicate the length of the graft cut by the cutting instrument.

Another one of the instruments used with the guide is a clamp which clamps the guide to the bone. The clamp includes a jaw pivotally mounted to the guide housing to grip the bone between the jaw and the bone-engaging portion of the guide. The surface of the jaw that engages the bone is ridged. The ridged surfaces of the jaw and the arms help ensure that the clamp securely retains the guide in place during cutting. The pivotal attachment between the jaw and the guide housing is provided by pins on the clamp which are received within slots in the housing. Preferably, the pins are differently-sized, as are the slots. This helps to avoid incorrectly assembling the clamp onto the guide housing.

The cutting instrument used with the guide is a saw. Preferably, the saw has a curved cutting surface. The saw also includes an elongated tube sized to be received within the opening in the guide. The saw and housing are configured to limit the motion of the curved cutting surface. This helps guard against excessive cutting.

The instruments are easy to use, and are particularly useful in cutting a bone graft from the patella, for example, during ACL replacement surgery.

In use, the initial cut is made in the bone surface with a saw in the selected orientation in which the bone graft is to be cut. Then, the bone-engageable portion (e.g., the flange) of the spacer is inserted into the cut. The surfaces of the spacer plate define the locations for the second (i.e., parallel) and third (i.e., transverse) saw cuts. The spacer is removed after the second and third cuts are made. Next, the bone-engaging portions (e.g., the rails) on the guide arms are inserted into the first and second, parallel cuts. This aligns the opening in the guide housing with the cuts, and hence with the selected orientation. The clamp is engaged to firmly grasp the patella between the jaw and the guide arms and secure the housing in position.

The cutting instrument (e.g., the saw with the curved cutting surface) is then inserted through the guide housing opening and rotated back and forth (e.g., by hand) to cut out the bone graft between the first and second cuts. The graft is completely separated from the underlying bone when the cutting instrument reaches the third, transverse cut.

The bone graft harvested with the invention is uniformly sized and has a smooth, rounded (e.g., convex) lower surface, and leaves a smooth, rounded (e.g., concave) depression in the patella. Accordingly, the graft requires little, if any, additional shaping before being inserted into the tibial or femoral tunnel. Moreover, because the graft is not removed by chiseling or the like (which tends to leave a V-shaped depression), the patella is subjected to reduced trauma and is less prone to fracturing. In this regard, the smooth-sided nature of the depression left in the patella minimizes the risk of so-called "stress risers" forming in the patella—one of the primary sources of fracturing.

Other features and advantages of the invention will become apparent from the following detailed description, and from the claims.

DRAWING

FIGS. 1A–1C show a set of instruments used in cutting a bone graft from the patella: a spacer (FIG. 1A), a guide and clamp (FIG. 1B), and a saw (FIG. 1C).

FIGS. 4A and 4B show additional details of the saw of FIG. 1C.

DESCRIPTION

Figure 2:
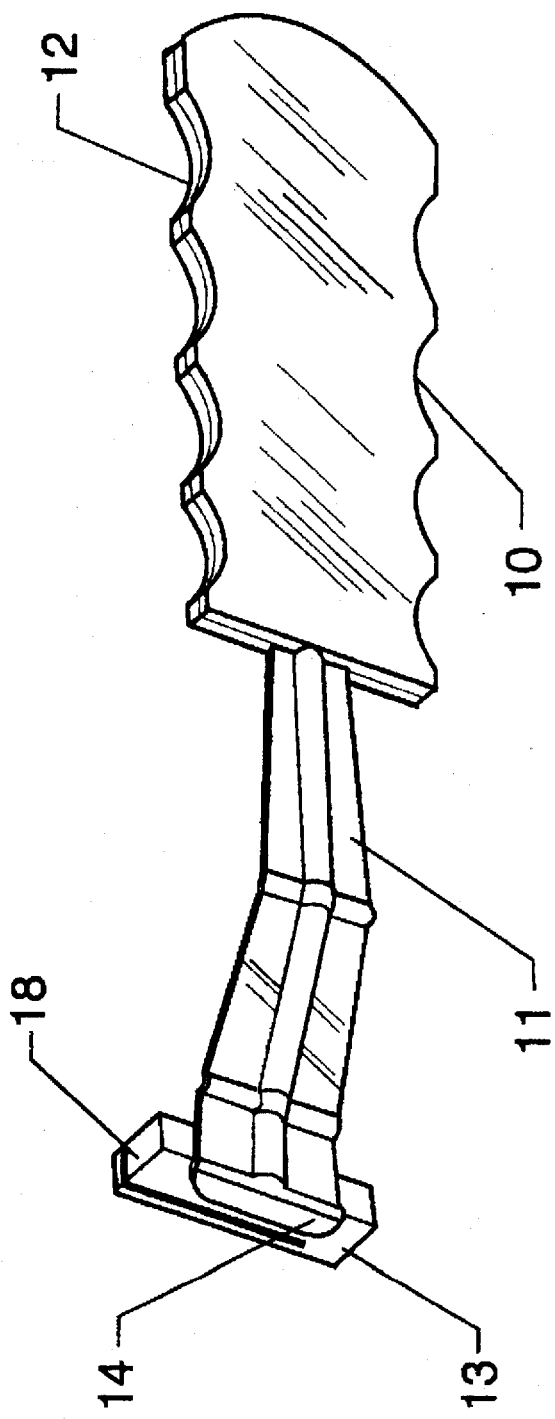
FIG. 2 shows the spacer of FIG. 1A in more detail.

FIGS. 1A–1C show a set of instruments—a spacer 10 (FIG. 1A), a guide 30 and clamp 50 (FIG. 1B), and a saw 70 (FIG. 1C)—for cutting a bone graft having a desired size and shape from the patella. The instruments are described in detail below, but briefly, spacer 10 is used to lay out the side and end boundaries of the bone graft and to direct a saw (not shown) in making side and end cuts in the patella that define the orientation of the bone graft. Guide 30 is mounted to the patella in the cuts defined by spacer 10 and secured in place with clamp 50. Saw 70 is inserted through, and directed by, guide 50 to cut the graft from the patella in the orientation defined by the side cuts.

Referring also to FIG. 2, spacer 10 includes a handle 12 which is connected to one side of a plate 13 by an arm 11. Arm 11 is angled so that handle 12 is perpendicular to plate 13 yet is offset from plate 13 to allow the upper surface of plate 13 to be clearly seen during use. A flange 14 protrudes from the lower surface of plate 13 beneath arm 11. Flange 14 is configured to be inserted into an initial, thin cut made in the patella by, e.g., an oscillating or sagittal saw, that defines the orientation of the bone graft and also one side of the graft. Accordingly, flange 14 is relatively thin and is tapered as it extends from plate 13 (e.g., from a thickness of 0.04 inch to a thickness of 0.01 inch) for ease of insertion into the cut. The increased thickness of flange 14 adjacent to plate 13 strengthens the flange. Flange 14 also has a length of about 0.88 inch and a height of about 0.13 inch. Arm 11, handle 12, plate 13, and flange 14 are made from metal and may be integrally formed (e.g., by casting) as a single piece of material.

A slot 16 is formed through plate 13 parallel to flange 14. Thus, with plate 13 placed on the patella and flange 14 inserted into the initial cut, the edges of slot 16 define the location for a second cut in the patella that will define the second side of the bone graft. The spacing between slot 16 and flange 14 is a function of the desired width of the bone graft. For example, flange 14 and slot 16 are spaced by 10 millimeters. Slot 16 is open at an end surface 18 of plate 13 to allow a saw (e.g., an oscillating or sagittal saw, not shown) to be inserted into slot 16 to make the second side cut. The opposite end of slot 16 is closed. Markings or other indicia 15 (such as a numerical scale) are provided on the upper surface of plate 13 to indicate the length of the bone graft.

Surface 18 is perpendicular to flange 14 and slot 16, and defines the location for a third cut that will define one end of the bone graft. That is, with flange 14 inserted into the initial cut, surface 18 is used to direct a saw (not shown) in accurately making the end cut perpendicular to the two side cuts discussed above.

Holes 20, 22 pass through plate 13 between the upper and lower surfaces thereof to expose corresponding regions of the patella. Holes 20, 22 are approximately centered between flange 14 and slot 16 and serve as guides through which suture holes may be accurately drilled in the graft before the graft is removed from the patella.

Figure 3A:
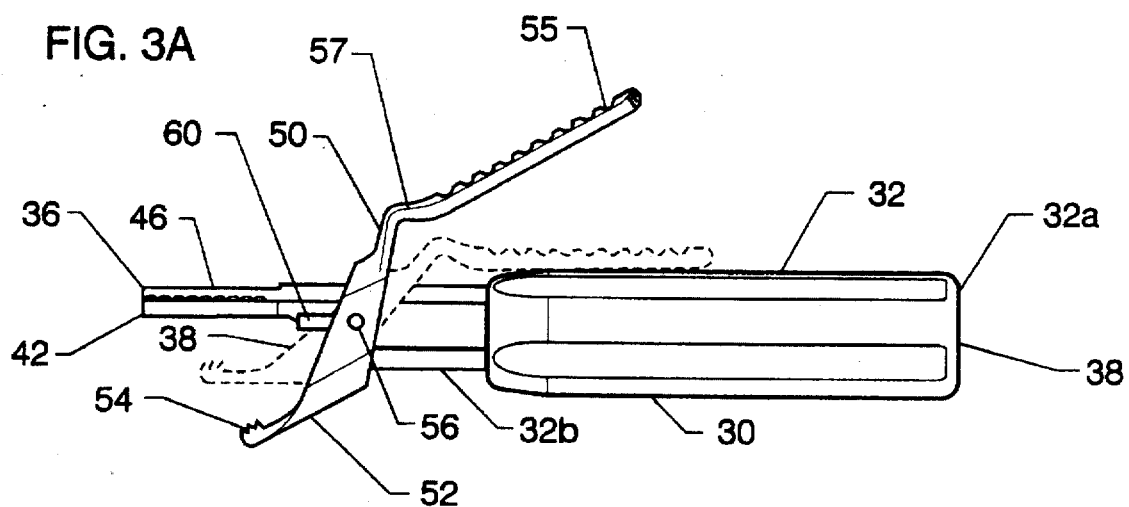
FIGS. 3A and 3B show additional views of the guide and clamp of FIG. 1B.
Figure 3B:
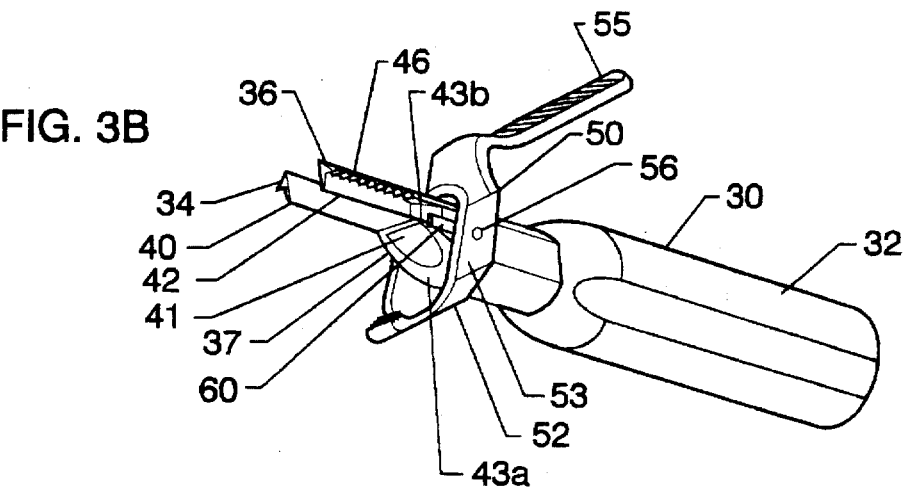

Referring to FIGS. 1B, 3A, and 3B, guide 30 includes a hollow metal housing 32 with an internal bore 38 that extends completely through housing 32 and is open at both the proximal end 32a and the distal end 32b of housing 32. A pair of arms 34, 36 extend axially from housing distal end 32b parallel to bore 38. A pair of thin rails 40, 42 are disposed on the undersides of arms 34, 36, respectively, parallel to bore 38. Rails 40, 42 are configured to be inserted into the two parallel side cuts defined by spacer 10 to accurately position bore 38 in the same orientation as the side cuts, all as discussed below. In addition, rails 40, 42 have approximately the same tapered configuration as flange 14. The spacing between rails 40, 42 corresponds to that between flange 14 and slot 16 of spacer 10 (FIGS. 1A and 2).

The undersides of arms 34, 36 adjacent to rails have roughened, ridged surfaces 46 which help grip the surface of the patella while the bone graft is being cut. The upper surfaces of arms 34, 36 are provided with markings or other indicia 35 (such as a numerical scale) to indicate the length of the bone graft. (Only ridged surface 46 and markings 35 of arm 36 are shown in FIG. 1B.)

Figure 3C:
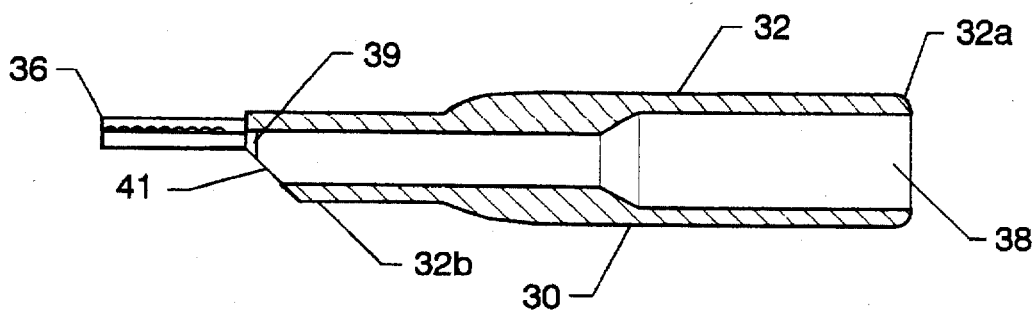
FIG. 3C shows a cross-sectional view of the guide of FIG. 3A.

Bore 38 is cylindrical from housing proximal end 32a to a shoulder 39 (FIG. 3C) located at the open distal end 41 of bore 38. The diameter of bore 38 is sized to engage saw 70 at distal end 32b, so that guide 30 will accurately direct saw 70 to cut the bone graft in the orientation defined by the engagement of guide rails 40, 42 in the patella side cuts. The diameter of bore 38 may be relatively larger at proximal end 32a than at distal end 32b, so that guide 30 is light and easy to hold. Due to shoulder 39, open distal end 41 of bore 38 appears semicircular with a curved lower surface 43a and a flat upper surface 43b (FIG. 3B) for purposes to be described.

The exterior surface of housing 32 includes a series of shallow axial channels 33 which facilitate grasping housing 32 during the bone cutting operation. Housing distal end 32b is narrower than the remainder of housing 32, and has a tapered end surface 37 which meets arms 34, 36. These features allow housing 32 to be positioned as closely as possible to the patella during graft cutting, as will be described below.

Clamp 50 is pivotally attached to guide housing 32 at distal end 32b slightly proximally of end surface 37. Clamp 50 includes a jaw 52 with a ridged surface 54 for gripping the underside of the patella, as discussed below, and a user-actuatable lever 55 for pivoting jaw 52 between the open position (shown in FIGS. 1B, 3A, and 3B) and the closed position (shown in dashed lines in FIG. 3A). An elbow 57 on lever 55 allows lever 55 to lie flat against housing 32 when jaw 52 is fully closed (FIG. 3A). Because lever 55 lies flat against housing 32, the clamp 50 and guide 30 may be held easily with one hand during graft cutting. In addition, elbow 57 provides a thumb rest and lever 55 has a textured upper surface to facilitate grasping by the user.

Jaw 52 and lever 55 are rigidly interconnected by a pair of arms 53 which are spaced from each other by an opening through which housing distal end 32b and arms 34, 36 extend. Jaw 52, arms 53, and lever 55 are made from metal and may be integrally formed as a single piece of material.

Clamp 50 is not permanently attached to housing 32. Rather, the user assembles clamp 50 onto housing 32 by sliding arms 53 over arms 34, 36 and housing distal end 32b to insert a pair of pins 56 on the interior surfaces of arms 53 into a corresponding pair of open-ended slots 60 in distal end 32b. (Only one each of pins 56 and slots 60 are shown.) The two pins 56 on respective arms 53 may be of different sizes (as may slots 60) to help guard against the user inadvertently assembling clamp 50 incorrectly onto housing 32 (e.g., with jaw 52 facing housing proximal end 32a rather than being positioned beneath arms 34, 36, as shown in the figures).

Referring to FIGS. 1C, 4A, and 4B, saw 70 includes an elongated tube 73 removably attached to a handle 72. The distal end of tube 73 is partially cut away to define a curved tongue 73a which meets tube 73 at shoulder 73b. The distal end of tongue 73a is serrated to form a curved cutting surface 74 (e.g., a segmented trephine blade). Tongue 73a, and hence cutting surface 74, extends along an arc of about 120 degrees and has a height H of about 0.11 inch (FIG. 4A).

Tube 73 is sized to be inserted into guide housing bore 38 at proximal end 32a and fits within bore 38 at distal end 32b with little side-to-side play, so that guide 30 will accurately direct saw 70 to cut the bone graft in the orientation defined by the engagement of guide rails 40, 42 in the patella side cuts. The length of tongue 73a and the position of bore shoulder 39 (FIG. 3C) are selected so that, when saw 70 is inserted into bore 38 and saw shoulder 73b engages bore shoulder 39, curved cutting surface 74 does not extend beyond (and preferably is coextensive with) guide arms 34, 36. This avoids cutting bone distally of arms 34, 36.

The semi-circular configuration of the open distal end 41 of bore 38 also limits the amount by which curved cutting surface 74 can be oscillated during cutting. That is, as tube 73 is rotated back and forth within bore 38, the flat upper surfaces of tongue 73a will engage flat surface 43b of bore 38 to prevent further rotation of cutting surface 74. The arc of curved cutting surface 74 may be varied, as desired. For example, cutting surface 74 may extend along arcs ranging from 120 degrees and 135 degrees. However, the arcs should be less than 180 degrees so that the curved cutting surface 74 may be oscillated back and forth by a meaningful amount within the open distal end 41 of bore 38 before meeting flat surface 43b.

A fitting 75 on the proximal end of tube 73 is removably attached to a collar 78 on handle 72. In particular, a pair of slots 76 (only one of which is shown) on fitting 75 receive correspond pins 80, 82 on the interior surface of collar 78 to ensure that cutting surface 74 is oriented properly with respect to handle 72. In addition, a set of so-called "ball locks" 84 (only one of which is shown) engage a circumferential groove 86 on fitting 75 to secure fitting 75 within collar 78. Ball locks are well known mechanisms and will not be described in detail. Suffice it to say that each ball lock 84 is spring-loaded to project into groove 86, and is retracted from groove 86 by sliding collar 78 proximally on handle 72. Accordingly, tube 73 may be detached from handle 72 for cleaning or discarded when cutting surface 74 becomes worn. In addition, tubes having different sizes (and hence smaller or larger cutting surfaces 74) may be used with handle 72.

Referring to FIGS. 5A–5D, the use of the instruments to remove a bone graft from the patella will now be described. First, an initial cut is made in the surface of the patella P using, e.g., an oscillating or sagittal saw 100. The initial cut defines one side of the patellar bone graft, as well as the orientation 102 in which the bone graft is to be cut. Typically, the orientation 102 of the graft is parallel to the length of the patella P between tibia T and femur F. Generally, the initial cut is made after a bone graft 104 has been cut from the tibia T and the middle one-third 106 of the patellar tendon 108 has been cut.

Figure 5B:
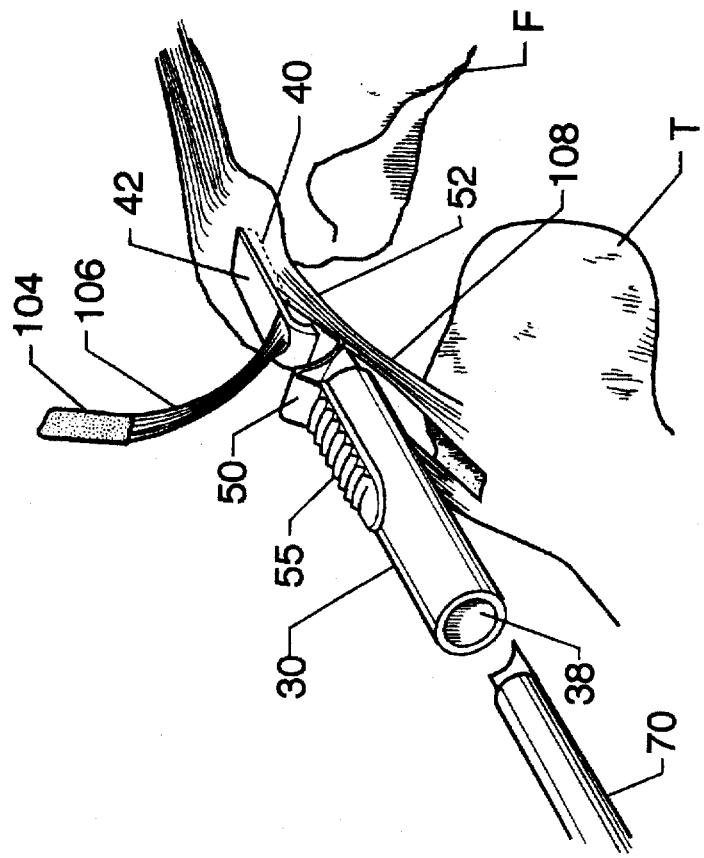
FIGS. 5A–5D illustrate using the instruments of FIGS. 1–4 to cut a bone graft from the patella.
Figure 5A:
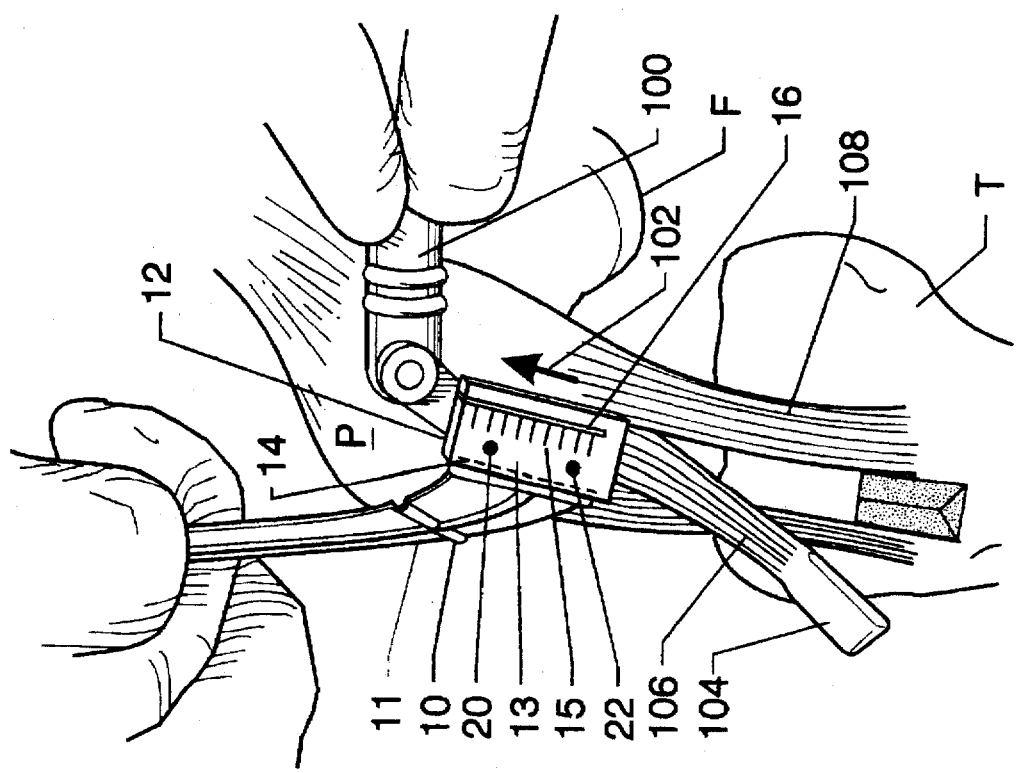

The user then grasps handle 12 of spacer 10 in one hand and inserts flange 14 into the initial cut so that plate 13 rests firmly on the surface of the patella P (FIG. 5A). Note that surface 18 and the open end of slot 16 face superiorly (i.e., toward the femur F). With his or her other hand, the user inserts saw 100 into slot 16, which directs saw 100 in making a second side cut in the patella P parallel to the initial cut and spaced from the initial cut as determined by the spacing between flange 14 and slot 16. Next, the user places saw 100 against surface 18 and makes the end cut in the patella. Surface 18 directs the saw so that the end cut is perpendicular to the initial cut and the second side cut and interconnects the initial cut and the second side cut on the superior side of the patella P.

The user may drill suture holes in the patella P between the side and end cuts via holes 20, 22. Of course, the suture holes may be drilled prior to making the side and end cuts. After all side and end cuts are made and the suture holes have been formed, spacer 10 is removed.

Next, clamp 50 is attached to guide 30 in the orientation shown in FIGS. 3A and 3B by inserting pins 56 into slots 60. Tibial bone graft 104 and patellar tendon strip 106 are pulled between guide arms 34, 36, and guide 30 and clamp 50 are inserted between the remaining portions of patellar tendon 108, i.e., from the inferior side of the patella P (FIG. 5B). Rails 40, 42 are placed within the initial and second side cuts to firmly engage the upper surface of the patella P. Then, by grasping lever 55 and housing 32 in one hand, the user pivots clamp 50 so that jaw 52 engages the underside of the patella P and clamps the patella P between arms 34, 36 and jaw 50. The ridged surfaces 46 of arms 34, 36 and the ridged surface 54 of jaw 50 helps ensure that guide 30 is securely held in place relative to the patella P.

With guide 30 clamped in place, bore 38 in housing 32 is positioned in the orientation defined by the initial and side cuts. Using his or her other hand, the user inserts saw 70 into bore 38 at the proximal end of housing 32 (FIGS. 5B, 5C), and advances saw 70 against the patella P. The user then manually oscillates saw 70 back and forth in a rotating motion to cause curved cutting surface 74 to make a rounded cut in the patella P, advancing from the inferior end of the side cuts to the transverse cut at the superior end of the side cuts. The bone graft being cut by saw 70 is disposed within the space defined by tongue 73a (FIG. 4A) so as not to interfere with continued cutting. Bore 38 directs saw 70 to cut the patella in the selected orientation defined by the side cuts. During the cutting operation, the user observes indicia 35 (FIG. 1B) to monitor the length of the graft.

Figure 5D:
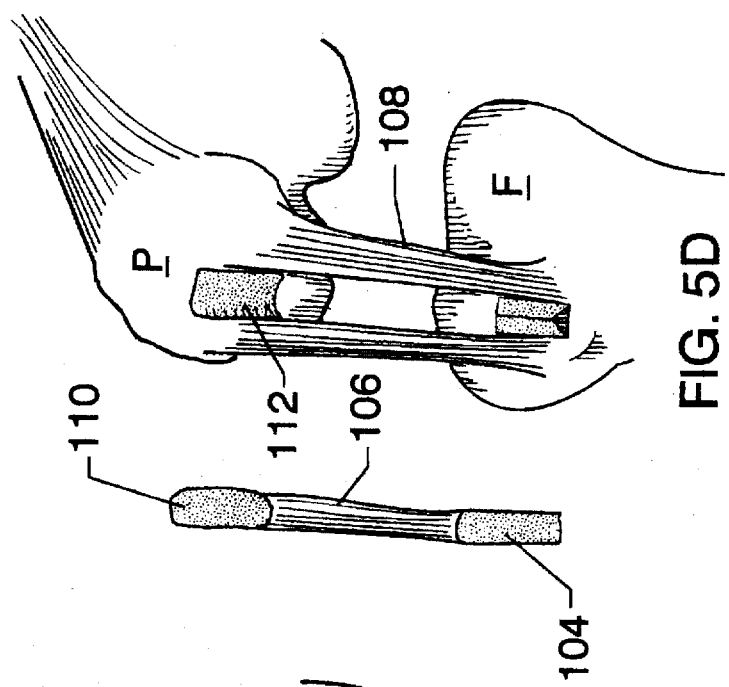
Figure 5C:
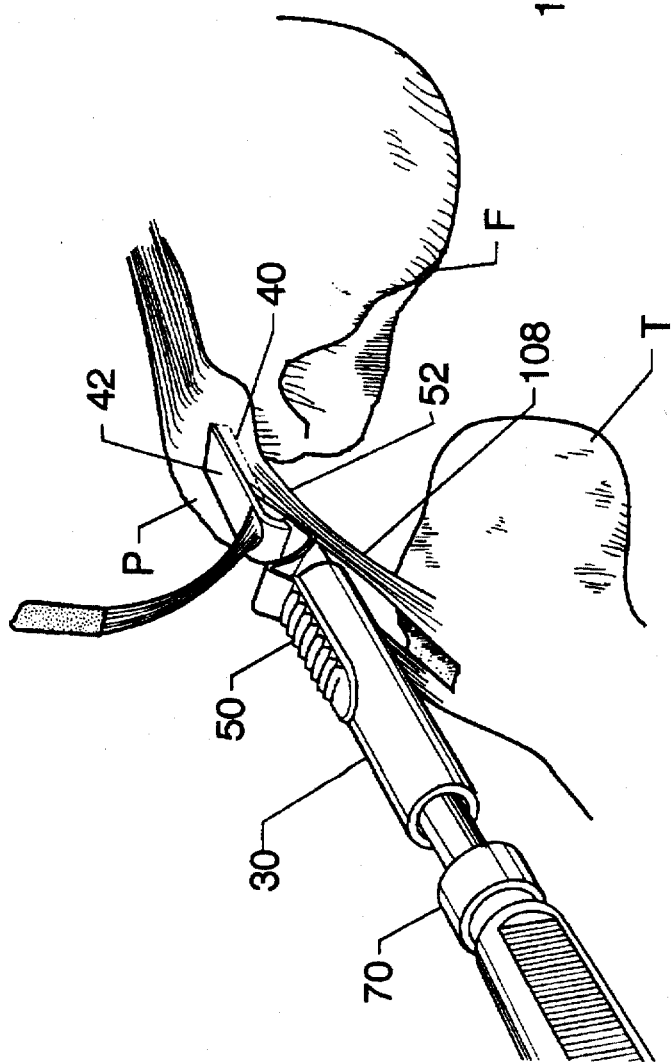

When curved cutting surface 74 reaches the transverse cut between the side cuts, the bone graft 110 is completely separated from the patella P, and can be removed (FIG. 5D). Bone graft 110 has a width defined by the spacing between the side cuts (and hence by the spacing between spacer flange 14 and slot 16). Due to the curved cut made by cutting surface 74, bone graft 110 has a smooth, rounded (e.g., convex) lower surface which meets the straight side cuts made by saw 100. As a result, graft 110 requires minimal, if any, post removal shaping before being inserted into tunnels (not shown) in the tibia T and femur F.

The depression 112 left behind in patella P when graft 110 is removed is smooth and rounded (e.g., concave). Thus, there is less risk that fracture-inducing stress risers will develop. The risk that the patella P will be fractured is further reduced due to the fact that bone graft 110 is removed by sawing, rather than by chiseling.

Other embodiments are within the scope of the following claims.

For example, the instruments may be provided in different sizes, depending on the desired size of the bone graft (e.g., 7 to 12 millimeters). A set of spacers 10, guides 30, and saw tubes 73 corresponding to various bone graft sizes may be provided. Each spacer would have a different amount of spacing between flange 14 and slot 16 corresponding to the associated bone graft size. The spacing between the rails 40, 42 and the diameters of the bores 38 of the guides 30 would likewise be selected to correspond to the various bone graft sizes, as would the diameters of the saw tubes 73. The set of guides 30 can advantageously have the same exterior dimensions to allow a single clamp 50 to be used with all guides 30.

In another embodiment, guide 30 may have an arm and rail configured to be inserted into the transverse side cut in the surface of the bone, rather than the parallel side cuts.

Although sawing the bone graft us desired to reduce the stress applied to the patella, an osteotome may be used in place of saw 70 to cut the graft in the orientation defined by the engagement of rails 40, 42 in the side cuts.

The instruments may be used to cut grafts from bones other than the patella.

There has been described novel and improved apparatus and techniques for cutting a bone graft. It is evident that those skilled in the art may now make numerous uses and modifications of and departures from the specific embodiments described herein without departing from the inventive concept.

What is claimed is:

1. Apparatus for cutting a graft from a bone, comprising:
    a bone cutting instrument;
    a spacer having a bone-engageable portion insertable into a first longitudinal cut in a surface of the bone and a surface configured to guide a saw in making a second longitudinal cut in a parallel orientation to said first longitudinal cut; and
    a guide for said bone cutting instrument, said guide comprising a guiding portion configured to engage said bone cutting instrument and at least one bone-engaging portion insertable into one of said first and second longitudinal cuts, wherein said bone-engaging portion positions said guiding portion in a selected orientation with respect to the bone and wherein said guiding portion directs said bone cutting instrument to cut the graft in the selected orientation.

2. The apparatus of claim 1 wherein said guide further comprises a second bone-engaging portion insertable into the other of said first and second longitudinal cuts in the bone surface.

3. The apparatus of claim 2 wherein said bone-engaging portions of said guide are arranged along said selected orientation so that said guiding portion directs said cutting instrument to cut the graft in the selected orientation between a first end of said first and second longitudinal cuts and a second end of said first and second longitudinal cuts in the bone surface.

4. The apparatus of claim 3 wherein said spacer further comprises a second surface arranged transversely to said bone-engageable portion and configured to guide a saw in making a third longitudinal cut in the bone surface transverse to the first-longitudinal cut and the second longitudinal cut at the second end thereof.

5. The apparatus of claim 1 wherein said spacer includes a plate to which said bone-engageable portion is attached, said surface being defined by an edge of a slot in said plate arranged parallel to said bone-engageable portion.

6. The apparatus of claim 5 wherein said bone-engageable portion includes a flange that protrudes from said plate.

7. The apparatus of claim 5 wherein said plate includes markings thereon adjacent to the slot to indicate the length of the second longitudinal cut.

8. The apparatus of claim 1 wherein said spacer includes a hole for exposing an area of bone surface under said spacer.

9. The apparatus of claim 1 wherein said guide includes a housing that supports said guiding portion and an arm secured to said housing, said bone-engaging portion being disposed on said arm.

10. The apparatus of claim 9 wherein said guiding portion includes an opening arranged in the selected orientation in said housing, and said arm extends from said housing along the selected orientation.

11. The apparatus of claim 10 wherein said bone-engaging portion includes a rail disposed on an underside of said arm, said underside having a ridged surface adjacent to said rail and engageable with the bone surface when said rail is inserted into one of said first and second longitudinal cuts.

12. The apparatus of claim 11 wherein said arm includes markings on an upper surface thereof for indicating a length of the graft cut by said bone cutting instrument.

13. The apparatus of claim 1 further comprising a clamp for clamping said guide to the bone.

14. The apparatus of claim 13 wherein said guide includes a housing that supports said guiding portion and an arm secured to said housing, said bone-engaging portion being disposed on an underside of said arm, said clamp including a jaw pivotally attached to said housing for gripping the bone between said jaw and said bone-engaging portion.

15. The apparatus of claim 14 wherein said jaw has a ridged surface for engaging the bone.

16. The apparatus of claim 14 wherein said clamp further includes a plurality of pins received within corresponding slots in said housing to provide the pivotal attachment.

17. The apparatus of claim 16 wherein said pins are of different sizes, and said slots are of different sizes.

18. The apparatus of claim 1 wherein said bone cutting instrument comprises a saw.

19. The apparatus of claim 18 wherein said saw has a curved cutting surface.

20. The apparatus of claim 18 wherein said guide includes a housing, said guiding portion includes a bore through said housing arranged in the selected orientation, and said saw includes an elongated tube sized to be received in said bore and having an end with a curved cutting surface.

21. The apparatus of claim 20 wherein said saw and said housing are configured to limit translation of said curved cutting surface.

22. A method of cutting a graft from a bone, comprising:
    making a first longitudinal cut in a surface of the bone to define a first side of the graft,
    inserting a portion of a spacer into said first longitudinal cut,
    using the spacer to define a region of the bone parallel to said first longitudinal cut at which a second longitudinal cut is to be made,
    making said second longitudinal cut using said spacer to define a second side of the graft parallel to said first side,
    inserting a bone-engaging portion of a guide into at least one of said first and second longitudinal cuts to position said guide in a selected orientation with respect to the bone, and cutting the bone with a cutting instrument and directing said cutting instrument with said guide so that said cutting instrument cuts the graft in the selected orientation.

23. The method of claim 22 wherein said guide includes a second bone-engaging portion and said guide inserting step includes inserting said second bone-engaging portion into said second longitudinal cut, and then performing said cutting and directing steps.

24. The method of claim 23 further comprising making the first-longitudinal cut and the second longitudinal cut along the selected orientation between a first end and a second end, and performing said cutting and directing steps so that the cutting instrument cuts the graft along the selected orientation between the first end and the second end of the first-longitudinal cut and the second longitudinal cut.

25. The method of claim 24 further comprising making a third longitudinal cut between the first-longitudinal cut and the second longitudinal cut at the second end thereof, and removing the graft from the bone after performing said cutting and directing steps.

26. The method of claim 22 further comprising clamping the guide to the bone during said cutting and directing steps.

27. The method of claim 22 wherein said cutting instrument is a saw and said cutting step includes sawing the bone.

28. The method of claim 27 wherein said saw has a curved cutting surface and said cutting step includes sawing a curved cut in the bone to define a curved side of said graft.

29. The method of claim 22 wherein the bone is a patella.

\* \* \* \* \*